(12) United States Patent
Chae et al.

(10) Patent No.: US 11,179,712 B2
(45) Date of Patent: Nov. 23, 2021

(54) METHOD FOR PREPARING SULFATED METAL OXIDE CATALYST FOR CHLORINATION, AND CHLORINATION METHOD USING SULFATED METAL OXIDE CATALYST

(71) Applicant: KOREA RESEARCH INSTITUTE OF CHEMICAL TECHNOLOGY, Daejeon (KR)

(72) Inventors: Ho Jeong Chae, Sejong (KR); Young Min Kim, Daejeon (KR); Jip Kim, Gumi-si (KR); Hyung Ju Kim, Sejong (KR)

(73) Assignee: KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 0 days.

(21) Appl. No.: 16/643,410

(22) PCT Filed: Aug. 30, 2018

(86) PCT No.: PCT/KR2018/010033
§ 371 (c)(1),
(2) Date: Feb. 28, 2020

(87) PCT Pub. No.: WO2019/045470
PCT Pub. Date: Mar. 7, 2019

(65) Prior Publication Data
US 2021/0069689 A1 Mar. 11, 2021

(30) Foreign Application Priority Data

Aug. 31, 2017 (KR) .................. 10-2017-0110831
Aug. 31, 2017 (KR) .................. 10-2017-0110848

(51) Int. Cl.
| | |
|---|---|
| *B01J 37/02* | (2006.01) |
| *B01J 6/00* | (2006.01) |
| *B01J 21/06* | (2006.01) |
| *B01J 37/04* | (2006.01) |
| *B01J 37/08* | (2006.01) |
| *C07C 17/06* | (2006.01) |
| *C07C 19/03* | (2006.01) |

(52) U.S. Cl.
CPC .......... *B01J 37/0201* (2013.01); *B01J 6/001* (2013.01); *B01J 21/066* (2013.01); *B01J 37/04* (2013.01); *B01J 37/08* (2013.01); *C07C 17/06* (2013.01); *C07C 19/03* (2013.01); *C07C 2521/06* (2013.01)

(58) Field of Classification Search
CPC ..... C07C 17/06; C07C 19/03; C07C 2521/06; B01J 21/066; B01J 23/14; B01J 35/1019; B01J 27/053; B01J 37/0201; B01J 6/001
See application file for complete search history.

(56) References Cited

U.S. PATENT DOCUMENTS

| | | |
|---|---|---|
| 4,769,504 A | 9/1988 | Noceti et al. |
| 5,087,786 A | 2/1992 | Nubel et al. |
| 2011/0201841 A1* | 8/2011 | Bowman ............... C07C 17/154 562/520 |

OTHER PUBLICATIONS

International Search Report of corresponding PCT Application No. PCT/KR2018/010033—6 pages (dated Dec. 10, 2018).
Alaya et al., "Surface acidity and catalytic activity of aged SO42—/SnO2 catalyst supported with WO3", Journal of Alloys and Compounds, vol. 575, No. 6—7 pages (2013).
Batamack et al., "Electrophilic chlorination of methane over superacidic sulfated zirconia", Catalysis Letters, vol. 25, Nos. 1-2—9 pages (1994).
Matsuhashi et al., "Solid Catalyst Treated with Anion: XIX. Synthesis of the Solid Superacid Catalyst of Tin Oxide Treated with Sulfate Ion", Applied Catalysis, vol. 59, No. 1—8 pages (1990).
Wang et al., "Advances in Methane Conversion Processes", Catalysis Today, vol. 285—12 pages (May 2017).
Yadav et al., "Preparation of highly superacidic sulfated zirconia via combustion synthesis and its application in Pechmann condensation of resorcinol with ethyl acetoacetate", Journal of Catalysis, vol. 292—12 pages (2012).
Zhang et al., "The Synthesis of Nano-Crystalline Metal Oxides by Solution Method", Nanocrystals—Synthesis, Characterization and Applications, Chapter 9—30 pages (2012).

* cited by examiner

*Primary Examiner* — Jafar F Parsa
(74) *Attorney, Agent, or Firm* — Knobbe Martens Olson & Bear LLP

(57) ABSTRACT

The present invention relates to a method for preparing a sulfated metal oxide catalyst for chlorination, and a method for producing a reaction product containing methyl chloride ($CH_3Cl$) by using the sulfated metal oxide catalyst. A sulfated zirconia catalyst and a sulfated tin oxide catalyst are disclosed as the sulfated metal oxide catalyst for chlorination.

10 Claims, 2 Drawing Sheets

METHOD FOR PREPARING SULFATED METAL OXIDE CATALYST FOR CHLORINATION, AND CHLORINATION METHOD USING SULFATED METAL OXIDE CATALYST

TECHNICAL FIELD

The present invention relates to a method for preparing a sulfated metal oxide catalyst for chlorination, and a method for producing a reaction product containing methyl chloride ($CH_3Cl$) by using the sulfated metal oxide catalyst.

More particularly, a first aspect of the present invention relates to a method for preparing a sulfated zirconia catalyst for chlorination, and a method for producing a reaction product containing methyl chloride ($CH_3Cl$) by using the sulfated zirconia catalyst.

More particularly, a second aspect of the present invention relates to a method for preparing a sulfated tin oxide catalyst for chlorination, and a method for producing a reaction product containing methyl chloride ($CH_3Cl$) by using the sulfated tin oxide catalyst.

BACKGROUND ART

Methyl chloride ($CH_3Cl$) may be used for producing light olefins such as ethylene and/or propylene by a reaction of chloromethane to olefin (CMTO).

Accordingly, recently, research on preparation of methyl chloride from natural gas, which is abundantly reserved, has also been constantly conducted, and in particular, research on a method for preparing methyl chloride from methane ($CH_4$), which is a main component of natural gas, has been actively conducted.

For example, WO 84/03277, U.S. Pat. Nos. 4,769,504 and 5,087,786, and the like disclose a method of activating methane by performing an oxychlorination reaction on methane using air and a chlorine compound. In the patent documents related to oxychlorination, contents of the preparation of methyl chloride by a reaction between methane, and air and chlorine gas on a supported catalyst in which copper or iron is used as a basic component are reported.

In addition, a synthetic reaction of methyl chloride by oxychlorination of methane has been studied by W. J. M. Pieters et al. (Appl. Catal., 11 (1984), 35), but it has been largely limited to commercial applications due to a problem on catalyst stability and a low yield, and research on an olefin synthetic process using the methyl chloride prepared by such a process has not received much attention.

In addition, papers such as J. Am. Chem. Soc., 107 (1985), 7097; Appl. Catal., 46 (1989), 251, Chem. Eng. Sci., (1994), 4617, and the like have reported a method in which copper is used a base catalyst, and a second metal is added to the base catalyst, and a method of adjusting a reaction pressure, in order to improve catalyst stability of an oxychlorination catalyst and a selectivity to methyl chloride.

However, in the above conventional methods related to the preparation of methyl chloride by oxychlorination of methane, a methane conversion and a selectivity to methyl chloride are not excellent, and a preparation process thereof is extremely complicated.

That is, there is a need for a method that may solve the process complexity by enabling exclusion of air as a reactant, implement a sufficiently excellent methane conversion and selectivity to methyl chloride, and improve the stability of a reaction catalyst to be used, when preparing methyl chloride from methane.

DISCLOSURE

Technical Problem

An object of a first aspect of the present invention is to prepare and provide a sulfated zirconia catalyst implementing an excellent selectivity to methyl chloride and having an improved stability, when being applied to a chlorination reaction. Another object of the first aspect of the present invention is to prepare a reaction product containing methyl chloride by using the sulfated zirconia catalyst.

An object of a second aspect of the present invention is to prepare and provide a sulfated tin oxide catalyst implementing a significantly excellent selectivity to methyl chloride when being applied to a chlorination reaction. Another object of the second aspect of the present invention is to prepare a reaction product containing methyl chloride by using the sulfated tin oxide catalyst.

Technical Solution

In order to achieve the above objects, a first aspect of the present invention provides a method for preparing a sulfated zirconia catalyst for chlorination, the method including:

a step a) of forming a mixed solution by mixing an amine reactant and a zirconium precursor containing an oxygen element and dissolving the mixture in a solvent;

a step b) of forming a gel-type product by heating and stirring the mixed solution formed in the step a);

a step c) of forming zirconia ($ZrO_2$) by calcining the gel-type product formed in the step b); and a step d) of preparing sulfated zirconia ($SO_4^{2-}/ZrO_2$) by impregnating the zirconia formed in the step c) with a solution containing a sulfated agent and evaporating the solvent by performing heating.

In addition, the first aspect of the present invention provides a sulfated zirconia catalyst for chlorination.

In addition, the first aspect of the present invention provides a method for producing a reaction product containing methyl chloride ($CH_3Cl$) by performing a chlorination reaction on a reactant containing methane ($CH_4$) under a presence of the sulfated zirconia catalyst for chlorination.

In order to achieve the above objects, a second aspect of the present invention provides a method for preparing a sulfated tin oxide ($SO_4^{2-}/SnO_2$) catalyst for chlorination, the method including:

a step a) of dissolving a tin precursor in a solvent and inducing hydrolysis of the tin precursor by adding aqueous ammonia until a pH of a solution reaches 7.5 or more;

a step b) of obtaining a solid product by filtering a precipitate obtained by the hydrolysis in the step a);

a step c) of producing tin hydroxide ($Sn(OH)_4$) by drying the solid product obtained in the step b);

a step d) of obtaining a solid product by impregnating the tin hydroxide ($Sn(OH)_4$) produced in the step c) with a solution containing a sulfated agent, stirring the solution and performing filtering;

a step e) of drying the solid product obtained in the step d); and a step f) of producing sulfated tin oxide by calcining the solid product dried in the step e).

In addition, the second aspect of the present invention provides a sulfated tin oxide catalyst for chlorination.

In addition, the second aspect of the present invention provides a method for producing a reaction product containing methyl chloride ($CH_3Cl$) by performing a chlorination reaction on a reactant containing methane ($CH_4$) under a presence of the sulfated tin oxide catalyst for chlorination.

Advantageous Effects

The sulfated zirconia catalyst according to the first aspect of the present invention significantly increases a methane conversion, implements a significantly excellent selectivity to methyl chloride, which is a product, and has a significantly excellent catalyst stability, when being applied to a chlorination reaction of methane. In addition, in the reaction by which methyl chloride is produced by using the sulfated zirconia catalyst according to the first aspect of the present invention, air is excluded as a reactant, and thus a simple process may be generally implemented.

The sulfated tin oxide catalyst for chlorination according to the second aspect of the present invention generally increases a methane conversion, and implements a significantly excellent selectivity to methyl chloride, which is a product, when being applied to a chlorination reaction of methane. In addition, in the reaction by which methyl chloride is produced by using the sulfated tin oxide catalyst according to the second aspect of the present invention, air is excluded as a reactant, and thus a simple process may be generally implemented.

BEST MODE

Figure 1:
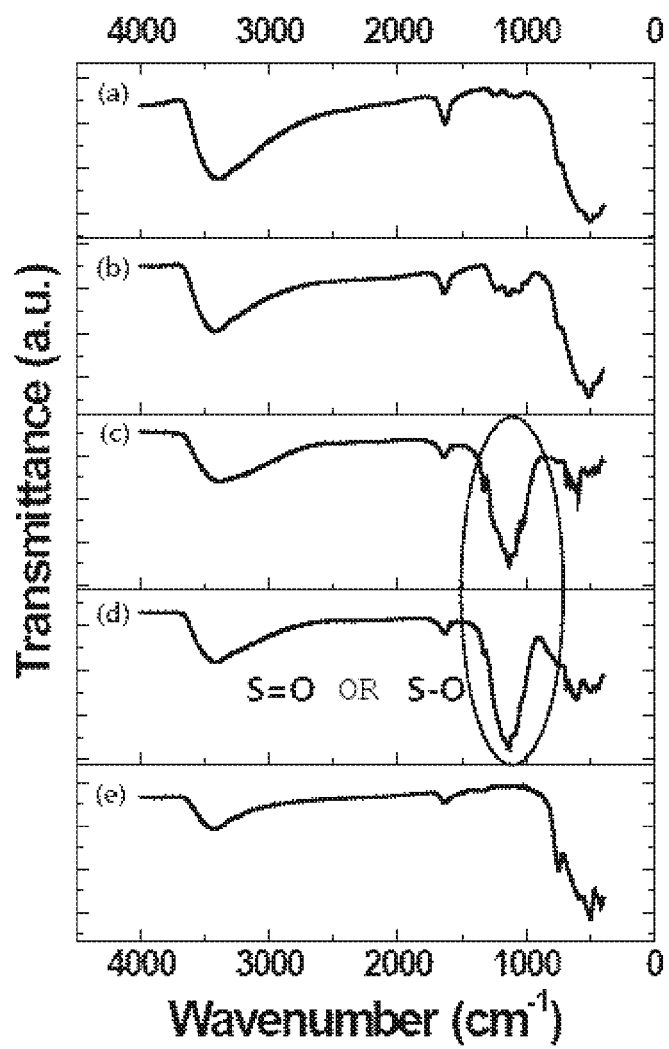
In FIG. 1, FIG. 1-(a) is a Fourier-transform infrared (FT-IR) spectrum of a catalyst of Comparative Example 1 collected after a chlorination reaction is applied, FIG. 1-(b) is an initial FT-IR spectrum of the prepared catalyst of Comparative Example 1, FIG. 1-(c) is an FT-IR spectrum of a catalyst of Example 1 collected after a chlorination reaction is applied, FIG. 1-(d) is an initial FT-IR spectrum of the prepared catalyst of Example 1, and FIG. 1-(e) is an FT-IR spectrum of zirconia powder, which is an intermediate material in a preparation process of Example 1.

Hereinafter, the present invention will be described in detail.

A first detailed aspect of a first aspect of the present invention provides a method for preparing a sulfated zirconia catalyst for chlorination, the method including:

a step a) of forming a mixed solution by mixing an amine reactant and a zirconium precursor containing an oxygen element (O) and dissolving the mixture in a solvent;

a step b) of forming a gel-type product by heating and stirring the mixed solution formed in the step a);

a step c) of forming zirconia ($ZrO_2$) by calcining the gel-type product formed in the step b); and a step d) of preparing sulfated zirconia ($SO_4^{2-}/ZrO_2$) by impregnating the zirconia formed in the step c) with a solution containing a sulfated agent and evaporating the solvent by performing heating.

Hereinafter, the method for preparing a sulfated zirconia catalyst for chlorination according to the first aspect of the present invention will be described in detail for each step.

In the step a), the amine reactant and the zirconium precursor containing an oxygen element are mixed preferably at a molar ratio of 1:0.5 to 1:5, and more preferably at a molar ratio of 1:1 to 1:3. The amine reactant is preferably selected from aspartic acid, glutamic acid, glycine, iminodiacetate, alanine, phenylalanine, isoleucine, histidine, lysine, arginine, and water-soluble salts thereof, but is not limited thereto as long as it is within a range in which the object of the present invention is achieved. The zirconium precursor containing an oxygen element is preferably selected from zirconyl chloride octahydrate ($ZrOCl_2 \cdot 8H_2O$) and zirconium(IV) oxynitrate hydrate ($ZrO(NO_3)_2 \cdot xH_2O$), but is not limited thereto as long as it is within a range in which the object of the present invention is achieved. A mixed solution is formed by dissolving the mixture formed according to the above in a solvent, and in this case, the mixture is dissolved in the solvent at a ratio of 0.5 to 5 ml mixture per gram of solvent. The solvent is preferably water. Specifically, distilled water, deionized water, or the like may be used as water in a non-limiting manner.

In the step b), a gel-type product is formed by heating and stirring the mixed solution formed in the step a). The heating temperature is preferably 60 to 100° C., and more preferably 70 to 90° C. The formed gel-type product has a high viscosity.

In the step c), zirconia ($ZrO_2$) is formed by calcining the gel-type product formed in the step b), and the formed zirconia is preferably a powder type. In this case, the calcination is preferably performed at 200 to 400° C., and more preferably performed at 300 to 400° C.

In the step d), sulfated zirconia ($SO_4^{2-}/ZrO_2$) is prepared by impregnating the zirconia formed in the step c) with a solution containing a sulfated agent and evaporating the solvent by performing heating. In this case, the zirconia is impregnated with the solution containing a sulfated agent at a ratio of 10 to 20 ml zirconia per gram of solution. In this case, the sulfated agent is preferably at least one selected from sulfuric acid, ammonium sulfate (($NH_4)_2SO_4$), and halosulfonic acid of the following Formula 1, but is not limited thereto as long as it is within a range in which the object of the present invention is achieved.

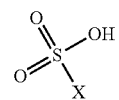

[Formula 1]

(Wherein X represents a halogen atom.)

As the halosulfonic acid of Formula 1, commercially available halosulfonic acid may be used, specifically, fluorosulfonic acid or chlorosulfonic acid may be used, and more preferably, chlorosulfonic acid may be used. In addition, in the solution containing a sulfated agent, a concentration of the sulfated agent is 0.1 M or more, more preferably 0.2 M or more, and most preferably 0.3 to 5 M. The heating temperature for evaporating the solvent may be adequately set depending on a solvent of a solution.

As one detailed aspect, the method for preparing a sulfated zirconia catalyst for chlorination according to the first detailed aspect of the first aspect of the present invention may further include a step e) of calcining the sulfated zirconia prepared in the step d) at 500 to 800° C. under an air atmosphere, in addition to the step d). In this case, the method for preparing a sulfated zirconia catalyst for chlorination may further include a step of drying the sulfated zirconia prepared in the step d) at 70 to 140° C. before the sulfated zirconia is calcined.

In addition, the preparation method according to the first detailed aspect of the first aspect of the present invention may further include a step f) of loading a transition metal other than Zr on the sulfated zirconia calcined in the step e) by impregnating the sulfated zirconia with a solution containing the transition metal other than Zr, evaporating the solvent, and then drying and calcining a residual product, in addition to the step e), while maintaining the one detailed aspect. The transition metal other than Zr is preferably at least one selected from Au, Sn, Pt, Ti, Fe, Ru, Ni, Cu, Al, and Mn, but is not limited thereto. In this case, in the solution containing the transition metal other than Zr, the transition metal other than Zr is present in a salt form. For example, $H_2PtCl_6 \cdot xH_2O$, $Fe(NO_3)_3$, $Mn(NO_3)_2$, or the like may be used in a salt form, but is not limited thereto. In addition, the drying after the solvent is evaporated is preferably performed at 70 to 140° C., and the calcination is preferably performed at 500 to 800° C. under an air atmosphere.

As another detailed aspect, the method for preparing a sulfated zirconia catalyst for chlorination according to the first detailed aspect of the first aspect of the present invention may further include: a step e) of drying the sulfated zirconia prepared in the step d) at 70 to 140° C.; and a step f) of loading a transition metal other than Zr on the sulfated zirconia dried in the step e) by impregnating the sulfated zirconia with a solution containing the transition metal other than Zr, evaporating the solvent, and drying and calcining a residual product, in addition to the step d). The transition metal other than Zr is preferably at least one selected from Au, Sn, Pt, Ti, Fe, Ru, Ni, Cu, Al, and Mn, but is not limited thereto. In this case, in the solution containing the transition metal other than Zr, the transition metal other than Zr is present in a salt form. For example, $H_2PtCl_6 \cdot xH_2O$, $Fe(NO_3)_3$, $Mn(NO_3)_2$, or the like may be used in a salt form, but is not limited thereto. In addition, the drying after the solvent is evaporated is preferably performed at 70 to 140° C., and the calcination is preferably performed at 500 to 800° C. under an air atmosphere.

A second detailed aspect of the first aspect of the present invention provides a sulfated zirconia catalyst for chlorination. The chlorination is preferably chlorination of a reactant containing methane, and more preferably chlorination of methane.

A content of sulfate ions ($SO_4^{2-}$) in the sulfated zirconia catalyst for chlorination is preferably 10.0 wt % or more, more preferably 20.0 wt % or more, and most preferably 24.0 to 37.0 wt %. When the content of the sulfate ions ($SO_4^{2-}$) in the sulfated zirconia catalyst is 10.0 wt % or more, the amount of the sulfate ions in the catalyst is sufficiently secured to sufficiently improve a very strong acidity of the catalyst, and thus the catalyst may be more applicable to a chlorination reaction.

A content of a sulfur element in the sulfated zirconia catalyst for chlorination is preferably 3.3 wt % or more, more preferably 6.6 wt % or more, and most preferably 8.0 to 12.3 wt %. When the content of the sulfur element in the sulfated zirconia catalyst for chlorination is 3.3 wt % or more, the amount of the sulfur element in the catalyst is sufficiently secured, and thus the catalyst may be more applicable to a chlorination reaction.

It is preferable that a total acid density of the sulfated zirconia catalyst for chlorination measured by ammonia temperature-programmed desorption ($NH_3$-TPD) is 8 mmol$NH_3$/g or more, and a proportion of an acid density of a very strong acid site (an acid site at which an acid site desorption temperature is higher than 400° C.) is 80% or more of the total acid density. It is more preferable that the total acid density of the sulfated zirconia catalyst for chlorination measured by ammonia temperature-programmed desorption ($NH_3$-TPD) is 10 mmol$NH_3$/g or more, and the proportion of the acid density of the very strong acid site (an acid site at which an acid site desorption temperature is higher than 400° C.) is 88% or more of the total acid density. It is most preferable that the total acid density of the sulfated zirconia catalyst for chlorination measured by ammonia temperature-programmed desorption ($NH_3$-TPD) is 12 to 15 mmol$NH_3$/g, and the proportion of the acid density of the very strong acid site (an acid site at which an acid site desorption temperature is higher than 400° C.) is 90 to 95% of the total acid density. In this case, the acid density is a measurement capable of quantifying an acid site of a catalyst, and is a numerical value capable of being measured by $NH_3$-TPD analysis. A weak acid site refers to an acid site at which an acid site desorption temperature is lower than 100° C., a medium acid site refers to an acid site at which the acid site desorption temperature is 100 to 200° C., a strong acid site refers to an acid site at which the acid site desorption temperature is 200 to 400° C., and a very strong acid site refers to an acid site at which the acid site desorption temperature is higher than 400° C. When the total acid density of the sulfated zirconia catalyst for chlorination of the present invention is 8 mmol$NH_3$/g or more, and the proportion of the acid density of the very strong acid site (an acid site at which an acid site desorption temperature is higher than 400° C.) is 80% or more of the total acid density, a very strong acidity of the catalyst is sufficiently secured, and electrophilic chlorination of the reactant is thus significantly promoted by the very strong acidity of the catalyst even at a low reaction temperature at the time of a chlorination reaction. As a result, a reactant conversion may also be significantly increased.

The sulfated zirconia catalyst for chlorination may be preferably prepared by the method of preparing a sulfated zirconia catalyst for chlorination according to the first detailed aspect of the first aspect of the present invention.

A third detailed aspect of the first aspect of the present invention provides a method for producing a reaction product containing methyl chloride ($CH_3Cl$) by performing a chlorination reaction on a reactant containing methane ($CH_4$) under a presence of the sulfated zirconia catalyst for chlorination. The reactant containing methane does not exclude a case where another material is additionally contained in addition to methane, and may be formed of only methane.

Specifically, the chlorination reaction is preferably performed: (i) at a temperature of 200 to 550° C.; (ii) at a molar ratio of the reactant containing methane to chlorine ($Cl_2$) gas of 1/1 to 10/1; and (iii) at a gas hourly space velocity (GHSV) of each of the reactants of 100 to 3000 cc/g/h. The chlorination reaction is more preferably performed: (i) at a temperature of 250 to 400° C.; (ii) at a molar ratio of the reactant containing methane to chlorine ($Cl_2$) gas of 1/1 to 3/1; and (iii) at a gas hourly space velocity (GHSV) of each of the reactants of 400 to 1000 cc/g/h.

In the chlorination reaction, distinctively, since air is not used as a reactant, the process complexity may be reduced as compared to the conventional oxychlorination reaction when preparing methyl chloride.

A first detailed aspect of a second aspect of the present invention provides a method for preparing a sulfated tin oxide ($SO_4^{2-}$/$SnO_2$) catalyst for chlorination, the method including:

a step a) of dissolving a tin precursor in a solvent and inducing hydrolysis of the tin precursor by adding aqueous ammonia until a pH of a solution reaches 7.5 or more;

a step b) of obtaining a solid product by filtering a precipitate obtained by the hydrolysis in the step a);

a step c) of producing tin hydroxide ($Sn(OH)_4$) by drying the solid product obtained in the step b);

a step d) of obtaining a solid product by impregnating the tin hydroxide ($Sn(OH)_4$) produced in the step c) with a solution containing a sulfated agent, stirring the solution and performing filtering;

a step e) of drying the solid product obtained in the step d); and a step f) of producing sulfated tin oxide by calcining the solid product dried in the step e).

Hereinafter, the method for preparing a sulfated tin oxide catalyst for chlorination according to the second aspect of the present invention will be described in detail for each step.

In the step a), a tin precursor is dissolved in a solvent, and then hydrolysis of the tin precursor is induced by adding aqueous ammonia until a pH of a solution reaches 7.5 or more. In this case, the tin precursor is dissolved in the solvent, and then the pH of the solution may be preferably adjusted to 8 to 12 by adding aqueous ammonia while stirring the solution at preferably room temperature. The tin precursor, which is a reactant, in the step a) is a tin precursor containing preferably a chlorine element (Cl), and more preferably at least one selected from $SnCl_2$, $SnCl_2 \cdot 2H_2O$, $CH_3(CH_2)_3SnCl_3$, $SnCl_4 \cdot 5H_2O$, and $SnCl_4$, but is not limited thereto as long as it is within a range in which the object of the present invention is achieved. The solvent is preferably water. Specifically, distilled water, deionized water, or the like may be used as water in a non-limiting manner.

In the step b), a solid product is obtained by filtering a precipitate obtained by the hydrolysis in the step a). The solid product obtained in this case may be washed with water, if necessary. As water, distilled water, deionized water, or the like may be used in a non-limiting manner, and distilled water may be more preferably used.

In the step c), tin hydroxide ($Sn(OH)_4$) is produced by drying the solid product obtained in the step b). In this case, the drying is preferably performed at 70 to 140° C., and more preferably performed at 90 to 120° C.

In the step d), a solid product is obtained by impregnating the tin hydroxide ($Sn(OH)_4$) produced in the step c) with a solution containing a sulfated agent, stirring the solution, and then performing filtering. In this case, the tin hydroxide ($Sn(OH)_4$) is impregnated with the solution containing a sulfated agent at a ratio of 10 to 20 ml tin hydroxide per gram of solution. In this case, the sulfated agent is preferably at least one selected from sulfuric acid, ammonium sulfate (($NH_4)_2SO_4$), and halosulfonic acid of the following Formula 1, but is not limited thereto as long as it is within a range in which the object of the present invention is achieved.

[Formula 1]

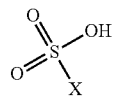

(Wherein X represents a halogen atom.)

As the halosulfonic acid of Formula 1, commercially available halosulfonic acid may be used, specifically, fluorosulfonic acid or chlorosulfonic acid may be used, and more preferably, chlorosulfonic acid may be used. In addition, in the solution containing a sulfated agent, a concentration of the sulfated agent is 0.1 M or more, more preferably 0.2 M or more, and most preferably 0.3 to 5 M.

In the step e), the solid product obtained in the step d) is dried. In this case, the drying is preferably performed at 70 to 140° C., and more preferably performed at 90 to 120° C. In addition, the solid product obtained in the step d) may be washed with water before being dried, if necessary. As water, distilled water, deionized water, or the like may be used in a non-limiting manner, and distilled water may be more preferably used.

In the step f), sulfated tin oxide, which is a final product, is produced by calcining the solid product dried in the step e). In this case, the calcination is preferably performed under an air atmosphere. The calcination temperature is preferably 300 to 700° C., and more preferably 400 to 600° C.

A second detailed aspect of the second aspect of the present invention provides a sulfated tin oxide catalyst for chlorination. The chlorination is preferably chlorination of a reactant containing methane, and more preferably chlorination of methane. A form of the catalyst is confirmed as a crystal form at the time of XRD analysis.

A content of sulfate ions ($SO_4^{2-}$) in the sulfated tin oxide catalyst for chlorination is preferably 5.0 wt % or more, more preferably 5.5 wt % or more, and most preferably 6.0 to 10.0 wt %. When the content of the sulfate ions ($SO_4^{2-}$) in the sulfated tin oxide catalyst is 5.0 wt % or more, the amount of the sulfate ions in the catalyst is sufficiently secured to sufficiently improve very strong acidity of the catalyst, and thus the catalyst may be more applicable to a chlorination reaction.

It is preferable that a total acid density of the sulfated tin oxide catalyst for chlorination measured by ammonia temperature-programmed desorption ($NH_3$-TPD) is 3.0 mmol$NH_3$/g or more, and a proportion of an acid density of a very strong acid site (an acid site at which an acid site desorption temperature is higher than 400° C.) is 50% or more of the total acid density. It is preferable that the total acid density of the sulfated tin oxide catalyst for chlorination measured by ammonia temperature-programmed desorption ($NH_3$-TPD) is 3.2 mmol$NH_3$/g or more, and the proportion of the acid density of the very strong acid site (an acid site at which an acid site desorption temperature is higher than 400° C.) is 52% or more of the total acid density. It is most preferable that the total acid density of the sulfated tin oxide catalyst for chlorination measured by ammonia temperature-programmed desorption ($NH_3$-TPD) is 3.3 to 5.0 mmol$NH_3$/g, and the proportion of the acid density of the very strong acid site (an acid site at which an acid site desorption temperature is higher than 400° C.) is 53 to 63% of the total acid density. In this case, the acid density is a measurement capable of quantifying an acid site of a catalyst, and is a numerical value capable of being measured by $NH_3$-TPD analysis. A weak acid site refers to an acid site at which an acid site desorption temperature is lower than 100° C., a medium acid site refers to an acid site at which the acid site desorption temperature is 100 to 200° C., a strong acid site refers to an acid site at which the acid site desorption temperature is 200 to 400° C., and a very strong acid site refers to an acid site at which the acid site desorption temperature is higher than 400° C. When the total acid density of the sulfated tin oxide catalyst for chlorination of the present invention is 3.0 mmol$NH_3$/g or more, and the proportion of the acid density of the very strong acid site (an acid site at which an acid site desorption temperature is higher than 400° C.) is 50% or more of the total acid density, the very strong acidity of the catalyst is sufficiently secured, and electrophilic chlorination of the reactant is significantly promoted by the very strong acidity of the catalyst even at a low reaction temperature at the time of a chlorination reaction. As a result, a reactant conversion may also be further increased.

A BET specific surface area of the sulfated tin oxide catalyst for chlorination is preferably 80 to 200 m²/g. When the sulfated tin oxide catalyst for chlorination is within the BET specific surface area range, a catalyst active site at which the reactant is adsorbable and desorbable at the time of a chlorination reaction is adequately secured, and thus the reactant conversion may be further increased.

The sulfated tin oxide catalyst for chlorination may be preferably prepared by the method of preparing a sulfated tin oxide catalyst for chlorination according to the first detailed aspect of the second aspect of the present invention.

A third detailed aspect of the second aspect of the present invention provides a method for producing a reaction product containing methyl chloride ($CH_3Cl$) by performing a chlorination reaction on a reactant containing methane ($CH_4$) under a presence of the sulfated tin oxide catalyst for chlorination. The reactant containing methane does not exclude a case where another material is additionally contained in addition to methane, and may be formed of only methane.

Specifically, the chlorination reaction is preferably performed: (i) at a temperature of 200 to 550° C.; (ii) at a molar ratio of the reactant containing methane to chlorine ($Cl_2$) gas of 1/1 to 10/1; and (iii) at a gas hourly space velocity (GHSV) of each of the reactants of 100 to 3000 cc/g/h. The chlorination reaction is more preferably performed: (i) at a temperature of 250 to 400° C.; (ii) at a molar ratio of the reactant containing methane to chlorine ($Cl_2$) gas of 1/1 to 3/1; and (iii) at a gas hourly space velocity (GHSV) of each of the reactants of 500 to 1500 cc/g/h.

In the chlorination reaction, distinctively, since air is not used as a reactant, the process complexity may be reduced as compared to the conventional oxychlorination reaction when preparing methyl chloride.

Hereinafter, the present invention will be described in detail with reference to Examples. However, the following Examples are merely provided to describe the present invention, and the contents of the present invention are not limited by the following Examples.

Comparative Example 1

Preparation of Sulfated Zirconia Catalyst for Chlorination by Method Different from Method of the Present Invention 30 g of $ZrOCl_2 \cdot 8H_2O$ (Aldrich) was dissolved in 300 ml deionized water, and then hydrolysis was induced by adding 28% aqueous ammonia until a pH of a solution reached 10 while stirring the solution at room temperature. At this time, a product was obtained by filtering a precipitate, the obtained product was sufficiently washed with distilled water, and then the washed product was placed in a drying oven and dried at 100° C. for 12 hours or longer, thereby producing zirconium hydroxide ($Zr(OH)_4$). A product was obtained by adding the produced zirconium hydroxide to a 0.5 M sulfuric acid solution at a ratio of 10 ml zirconium hydroxide per gram of sulfuric acid solution, stirring the solution for 1 hour, and then performing filtering. The obtained product was washed with distilled water, and then the washed product was placed in a drying oven and dried at 100° C. for 12 hours or longer. The dried product was placed in an electric furnace, and then calcined at 600° C. for 3 hours under an air atmosphere, thereby obtaining 6 g of a final product. A content of sulfate ions ($SO_4^{2-}$) in the produced final product was 5.2 wt %, and the content of the sulfate ions was measured by Thermogravimetric Analysis (TGA).

An acid density of the produced final product was measured by integrating an acid strength distribution measured by ammonia temperature-programmed desorption ($NH_3$-TPD). The measurement method is as follows. After 50 mg of the final product was heated at 300° C. for 1 hour under He gas, ammonia was adsorbed to the heated final product at 100° C. for 1 hour, and then sweeping was performed with He gas at 50° C. for 1 hour. The temperature was raised under He gas, and desorbed ammonia was measured with a thermal conductivity detector (TCD).

A density of weak acid was evaluated by measuring ammonia desorbed in a range of lower than 100° C., a density of medium acid was evaluated by measuring ammonia desorbed in a range of 100 to 200° C., a density of strong acid was evaluated by measuring ammonia desorbed in a range of 200 to 400° C., and a density of very strong acid was evaluated by measuring ammonia desorbed in a range of higher than 400° C. The results are shown in [Table 1]. A proportion of the acid density of the very strong acid site (an acid site at which an acid site desorption temperature is higher than 400° C.) was about 63% of a total acid density.

TABLE 1

| Reaction catalyst | Acid density (mmol$NH_3$/g) | | | | |
| --- | --- | --- | --- | --- | --- |
| | Weak acid | Medium acid | Strong acid | Very strong acid | Total |
| Comparative Example 1 | 0.061 | 0.490 | 0.693 | 2.083 | 3.327 |

A Fourier-transform infrared (FT-IR) spectrum of the produced final product corresponds to FIG. 1-(b).

First, in FIG. 1-(b), it is analyzed that a characteristic peak near 1032 and 1130 cm$^{-1}$ shows a S=O or S—O bond of loaded sulfate ions ($SO_4^{2-}$).

In addition, in FIG. 1-(b), it is analyzed that a peak in a range of 3000 to 3500 cm$^{-1}$ is generated due to physical adsorption of moisture in the atmosphere to a surface of the produced final product, and it is analyzed that a peak near 1625 cm$^{-1}$ is generated due to a hydroxyl group (—OH) formed on the surface of the final product, the hydroxyl group being generated by a reaction between the surface of the final product and moisture in the atmosphere. That is, it is analyzed that a sulfated zirconia catalyst, which is the final product, of Comparative Example 1, has reactivity with moisture in the atmosphere under an air atmosphere.

Example 1

Preparation of Sulfated Zirconia Catalyst for Chlorination by Method of the Present Invention 2 g of glycine (Aldrich) and 12.32 g of $ZrO(NO_3)_2 \cdot xH_2O$ (Aldrich) were mixed at a molar ratio of 1:2, and then the mixture was dissolved in distilled water at a ratio of 2 ml mixture per gram of distilled water, thereby forming an aqueous solution. The formed aqueous solution was stirred at 80° C. for 2 hours, thereby forming a gel-type product having a high viscosity. The gel-type product was placed in an electric furnace, and then calcined at 350° C. for 3 hours, thereby forming zirconia ($ZrO_2$) powder. An FT-IR spectrum of the formed zirconia powder corresponds to FIG. 1-(e). It is analyzed that a characteristic peak in a range of 460 to 850 $cm^{-1}$ shows the presence of a Zr—O—Zr bond. The formed zirconia powder was impregnated with a 1 M chlorosulfonic acid/ethylene dichloride solution at a ratio of 15 ml zirconia powder per gram of 1 M chlorosulfonic acid/ethylene dichloride solution, and then a solvent was evaporated by performing heating at 120° C. for 24 hours. After the solvent was evaporated, the residual product was placed in an electric furnace, and then calcined at 650° C. for 3 hours under an air atmosphere, thereby obtaining 3.6 g of a final product. A content of sulfate ions ($SO_4^{2-}$) in the produced final product was 32.2 wt %, and the content of the sulfate ions was measured by Thermogravimetric Analysis (TGA).

An acid density of the prepared final product was measured by integrating an acid strength distribution measured by ammonia temperature-programmed desorption ($NH_3$-TPD). The measurement method is as follows. After 50 mg of the final product was heated at 300° C. for 1 hour under He gas, ammonia was adsorbed to the heated final product at 100° C. for 1 hour, and then sweeping was performed with He gas for 1 hour. The temperature was raised under He gas, and desorbed ammonia was measured with a thermal conductivity detector (TCD).

A density of weak acid was evaluated by measuring ammonia desorbed in a range of lower than 100° C., a density of medium acid was evaluated by measuring ammonia desorbed in a range of 100 to 200° C., a density of strong acid was evaluated by measuring ammonia desorbed in a range of 200 to 400° C., and a density of very strong acid was evaluated by measuring ammonia desorbed in a range of higher than 400° C. The results are shown in [Table 2]. A proportion of the acid density of the very strong acid site (an acid site at which an acid site desorption temperature is higher than 400° C.) was about 92% of a total acid density.

TABLE 2

| Reaction catalyst | Acid density (mmol$NH_3$/g) | | | | |
|---|---|---|---|---|---|
| | Weak acid | Medium acid | Strong acid | Very strong acid | Total |
| Example 1 | 0.041 | 0.250 | 0.786 | 12.177 | 13.254 |

An FT-IR spectrum of the produced final product corresponds to FIG. 1-(d).

First, in FIG. 1-(d), it is analyzed that a characteristic peak near 1032 and 1130 $cm^{-1}$ shows a S=O or S—O bond of loaded sulfate ions ($SO_4^{2-}$), and a strength of the peak is significantly higher than in the case of the sulfated zirconia catalyst of Comparative Example 1. Therefore, it is analyzed that in the case of the sulfated zirconia catalyst of the present invention prepared by Example 1, more sulfate ionic groups are formed as compared to the case of the catalyst of Comparative Example 1.

In addition, in FIG. 1-(d), it is analyzed that a peak of a range of 3000 to 3500 $cm^{-1}$ is generated due to physical adsorption of moisture in the atmosphere to a surface of the produced final product, and it is analyzed that a peak near 1625 $cm^{-1}$ is generated due to a hydroxyl group (—OH) formed on the surface of the final product, the hydroxyl group being generated by a reaction between the surface of the final product and moisture in the atmosphere. That is, it is analyzed that a sulfated zirconia catalyst, which is the final product, of the present invention, has reactivity with moisture in the atmosphere under an air atmosphere.

In addition, in FIG. 1-(d), it is analyzed that a peak in a range of 460 to 850 $cm^{-1}$ shows the presence of a Zr—O—Zr bond in the final product.

Experimental Example 1

A chlorination reaction was performed by reacting methane with chlorine gas by using the sulfated zirconia catalysts prepared by Comparative Example 1 and Example 1.

The chlorination reaction was performed in a fixed bed reactor (length of 450 mm, inner diameter of 11 mm, Inconel tube reactor), and the reaction conditions were adopted as follows: (i) a temperature of 300° C.; (ii) a molar ratio of methane to chlorine gas of 2/1; and (iii) a gas hourly space velocity (GHSV) of each of methane and chlorine gas of 500 cc/g/h. A chlorine gas path in the reactor was shielded, and products produced by the chlorination reaction were analyzed by using gas chromatography (GC) using a HP PLOT-Q capillary column and a flame ionization detector (GC-FID). A methane conversion and a selectivity to products (chlorinated products of methane) are shown in [Table 3].

TABLE 3

| Reaction catalyst | $CH_4/Cl_2$ (Molar ratio) | GHSV (cc/g/h) | Reaction temperature (° C.) | Methane conversion (%) | Selectivity to product(%) | | | |
|---|---|---|---|---|---|---|---|---|
| | | | | | $CH_3Cl$ | $CH_2Cl_2$ | $CHCl_3$ | $CCl_4$ |
| None | 2/1 | 500 | 300 | 3.3 | 94.6 | 5.4 | 0 | 0 |
| Comparative Example 1 | 2/1 | 500 | 300 | 6.2 | 92.9 | 7.1 | 0 | 0 |
| Example 1 | 2/1 | 500 | 300 | 13.6 | 83.1 | 16.9 | 0 | 0 |

According to [Table 3], it is confirmed that, when the chlorination reaction of methane was performed by using the sulfated zirconia catalyst of Example 1 according to the present invention, the methane conversion was significantly increased, and the selectivity to methyl chloride, which is a product, was also sufficiently excellent.

Further, after the chlorination reaction of methane, the sulfated zirconia catalysts obtained by Comparative Example 1 and Example 1 were collected, FI—IR spectra of the collected catalysts were observed, and contents of sulfur elements were also measured.

First, FIG. 1-(a) shows the collected catalyst of Comparative Example 1, and it is observed that a peak strength, in particular, near 1032 and 1130 $cm^{-1}$, was significantly reduced than before the reaction (FIG. 1-(b)). However, FIG. 1-(c) shows the collected catalyst of Example 1, and it is observed that a peak strength near 1032 and 1130 cm$^{-1}$ was not significantly reduced than before the reaction (FIG. 1-(d)).

Further, the contents of the sulfur elements before and after the chlorination reactions of the sulfated zirconia catalysts obtained by Comparative Example 1 and Example 1 were confirmed as shown in [Table 4]. The content of the sulfur element of the catalyst was measured with an elemental analyzer (EA).

TABLE 4

| Reaction catalyst | Content of sulfur element (wt %) | |
| --- | --- | --- |
| | Before chlorination reaction | After chlorination reaction |
| Comparative Example 1 | 1.5 | 0.4 |
| Example 1 | 11.8 | 8.6 |

According to [Table 4], it is observed that the content of the sulfur element of the catalyst of Comparative Example 1 after the catalyst was used for the chlorination reaction was significantly reduced by less than half. However, a significant decrease of the content of the sulfur element of the catalyst of Example 1 even after the catalyst was used for the chlorination reaction was not observed.

Therefore, according to FIG. 1 and [Table 4], it is confirmed that the stability of the catalyst of Example 1 according to the present invention was significantly improved as compared to that of the catalyst of Comparative Example 1, as long as the catalyst was not significantly changed even after the catalyst of Example 1 was used for the chlorination reaction.

Example 2

Preparation of Sulfated Tin Oxide Catalyst for Chlorination by Method of the Present Invention 25 g of tin chloride pentahydrate (SnCl$_4$.5H$_2$O) was dissolved in 500 ml distilled water, and then hydrolysis of SnCl$_4$.5H$_2$O was induced by adding aqueous ammonia (28%) until a pH of a solution reached 8 while stirring the solution at room temperature. At this time, a solid product was obtained by filtering a precipitate obtained by the hydrolysis, the obtained solid product was sufficiently washed with distilled water, and then the washed product was placed in a drying oven and dried at 110° C. for 12 hours or longer, thereby producing 5.5 g of tin hydroxide (Sn(OH)$_4$). The produced tin hydroxide (Sn(OH)$_4$) was impregnated with a sulfuric acid solution (concentration of sulfuric acid: 0.5 M) at a ratio of 15 ml tin hydroxide per gram of sulfuric acid solution, the solution was stirred for 1 hour, and then filtering was performed, thereby obtaining a solid product. The obtained solid product was washed with distilled water, and then the washed product was placed in a drying oven and dried at 110° C. for 2 hours. The dried solid product was placed in an electric furnace, and then calcined at 500° C. for 3 hours under an air atmosphere, thereby obtaining 4.8 g of a final product. A content of sulfate ions (SO$_4^{2-}$) in the produced final product was measured by Thermogravimetric Analysis (TGA). The measured content is 6.1 wt %.

Example 3

Preparation of Sulfated Tin Oxide Catalyst for Chlorination by Method of the Present Invention 5.2 g of a final product was produced by using the same manner as that of Example 2, except that a concentration of a sulfuric acid in a sulfuric acid solution with which the produced tin hydroxide (Sn(OH)$_4$) was impregnated was 1 M. A content of sulfate ions (SO$_4^{2-}$) in the final product was 6.8 wt %.

Example 4

Preparation of Sulfated Tin Oxide Catalyst for Chlorination by Method of the Present Invention 5.3 g of a final product was produced by using the same manner as that of Example 2, except that a concentration of a sulfuric acid in a sulfuric acid solution with which the produced tin hydroxide (Sn(OH)$_4$) was impregnated was 2 M. A content of sulfate ions (SO$_4^{2-}$) in the final product was 7.9 wt %.

Example 5

Preparation of Sulfated Tin Oxide Catalyst for Chlorination by Method of the Present Invention 5.4 g of a final product was produced by using the same manner as that of Example 2, except that a concentration of a sulfuric acid in a sulfuric acid solution with which the produced tin hydroxide (Sn(OH)$_4$) was impregnated was 3 M. A content of sulfate ions (SO$_4^{2-}$) in the final product was 8.4 wt %.

<Observation of Characteristics of Sulfated Tin Oxide Catalyst Prepared by Examples>

(1) Fourier-Transform Infrared Spectroscopy (FT-IR) Analysis

Figure 2:
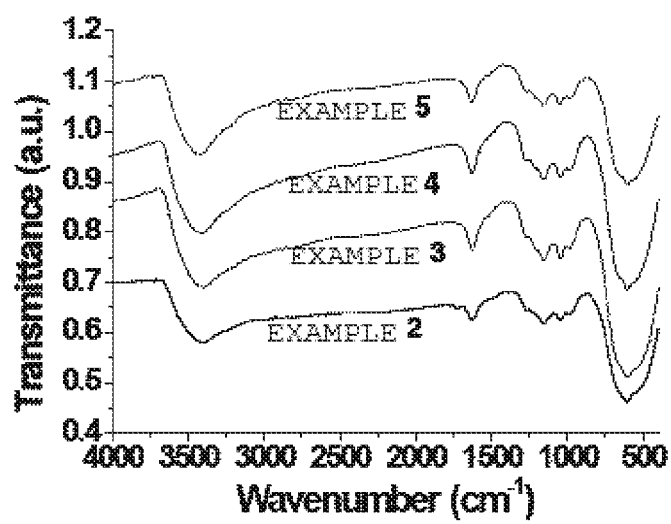
FIG. 2 shows FT-IR spectra of sulfated tin oxide catalysts for chlorination of Examples 2 to 5.

The FT-IR spectra of the sulfated tin oxide catalysts, which are final products, prepared by Examples 2 to 5 correspond to FIG. 2.

In FIG. 2, it is analyzed that a characteristic peak in a range of 900 to 1200 cm$^{-1}$ shows a S=O and S—O bond (a SO$_4^{2-}$ group) of loaded sulfate ions.

In addition, in FIG. 2, it is analyzed that a peak of a range of 3200 to 3600 cm$^{-1}$ is generated due to physical adsorption of moisture in the atmosphere to a surface of the produced final product, and it is analyzed that a peak near 1628 cm$^{-1}$ is generated due to a hydroxyl group (—OH) formed on the surface of the final product, the hydroxyl group being generated by a reaction between the surface of the final product and moisture in the atmosphere. That is, it is analyzed that a sulfated tin oxide catalyst, which is the final product, of the present invention, has reactivity with moisture in the atmosphere under an air atmosphere.

In addition, in FIG. 2, it is analyzed that a peak in a range of 600 to 620 cm$^{-1}$ shows the presence of a Sn—O—Sn bond in the final product.

(2) X-Ray Diffraction (XRD) Analysis

XRD analysis was performed to confirm the presence or absence of crystal formation in the sulfated tin oxide catalysts, which are final products, prepared by Examples 2 to 5, and what substance the crystal is formed of. The results are shown in FIG. 3.

Figure 3:
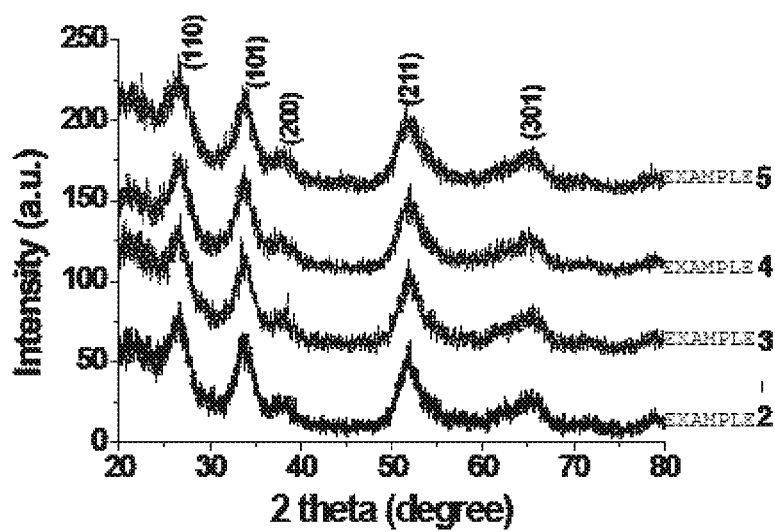
FIG. 3 shows XRD analysis results of the sulfated tin oxide catalysts for chlorination of Examples 2 to 5.

According to FIG. 3, XRD patterns of the sulfated tin oxide catalysts of Examples 2 to 5 are the same as each other. From the results of XRD library search, it can be appreciated that the XRD patterns are tetragonal SnO$_2$ crystal forms.

(3) BET Specific Surface Area Analysis

BET specific surface areas of the sulfated tin oxide catalysts, which are final products, prepared by Examples 2 to 5 were measured with a N$_2$ adsorptive specific surface area analyzer (manufacturer: Micromeritics, model name: Tristar 3000). The results are shown in [Table 5].

TABLE 5

| Catalyst | BET specific surface area (m²/g) |
|---|---|
| Example 2 | 102.3 |
| Example 3 | 113.6 |
| Example 4 | 128.8 |
| Example 5 | 137.6 |

(4) Ammonia Temperature-Programmed Desorption ($NH_3$-TPD) Analysis

Acid densities of the sulfated tin oxide catalysts, which are final products, prepared by Examples 2 to 5 were measured by integrating an acid strength distribution measured by ammonia temperature-programmed desorption ($NH_3$-TPD). The measurement methods are as follows. After 50 mg of the final product was heated at 300° C. for 1 hour under He gas, ammonia was adsorbed to the heated final product at 100° C. for 1 hour, and then sweeping was performed with He gas for 1 hour. The temperature was raised under He gas, and desorbed ammonia was measured with a thermal conductivity detector (TCD).

A density of weak acid was evaluated by measuring ammonia desorbed in a range of lower than 100° C., a density of medium acid was evaluated by measuring ammonia desorbed in a range of 100 to 200° C., a density of strong acid was evaluated by measuring ammonia desorbed in a range of 200 to 400° C., and a density of very strong acid was evaluated by measuring ammonia desorbed in a range of higher than 400° C. The results are shown in [Table 6].

TABLE 6

| | Acid density (mmol$NH_3$/g) | | | | | Proportion of very strong acid/total |
|---|---|---|---|---|---|---|
| Catalyst | Weak acid | Medium acid | Strong acid | Very strong acid | Total | |
| Example 2 | 0.069 | 0.805 | 0.709 | 1.910 | 3.493 | 55% |
| Example 3 | 0.083 | 0.793 | 0.776 | 2.428 | 4.08 | 60% |
| Example 4 | 0.094 | 0.969 | 0.890 | 2.489 | 4.442 | 56% |
| Example 5 | 0.075 | 0.924 | 0.937 | 2.705 | 4.641 | 58% |

Experimental Example 2

A chlorination reaction was performed by reacting methane with chlorine gas by using 0.5 g of each of the sulfated tin oxide catalysts prepared by Examples 2 to 5.

The chlorination reaction was performed in a fixed bed reactor (length of 450 mm, inner diameter of 11 mm, Inconel tube reactor). A chlorine gas path in the reactor was shielded, and products produced by the chlorination reaction were analyzed by using gas chromatography (GC) using a HP PLOT-Q capillary column and a flame ionization detector (GC-FID). A methane conversion and a selectivity to products (chlorinated products of methane) are shown in [Table 7].

TABLE 7

| Reaction catalyst | $CH_4/Cl_2$ (molar ratio) | GHSV (cc/g/h) | Reaction temperature (° C.) | Methane conversion (%) | Selectivity to product (%) | | | |
|---|---|---|---|---|---|---|---|---|
| | | | | | $CH_3Cl$ | $CH_2Cl_2$ | $CHCl_3$ | $CCl_4$ |
| None | 1.5/1 | 1000 | 300 | 3.4 | 95.2 | 4.8 | — | — |
| | | | 325 | 9.3 | 88.7 | 11.3 | — | — |
| | | | 350 | 17.1 | 78.7 | 19.0 | 2.3 | — |
| Example 2 | 1.5/1 | 1000 | 300 | 4.2 | 100 | — | — | — |
| | | | 325 | 10.2 | 97.6 | 2.4 | — | — |
| | | | 350 | 16.0 | 96.2 | 3.8 | — | — |
| Example 3 | 1.5/1 | 1000 | 300 | 4.3 | 100 | — | — | — |
| | | | 325 | 11.9 | 97.6 | 2.4 | — | — |
| | | | 350 | 18.8 | 96.7 | 3.3 | — | — |
| Example 4 | 1.5/1 | 1000 | 300 | 4.4 | 100 | — | — | — |
| | | | 325 | 12.4 | 98.0 | 2.0 | — | — |
| | | | 350 | 20.1 | 96.2 | 3.8 | — | — |
| Example 5 | 1.5/1 | 1000 | 300 | 5.1 | 100 | — | — | — |
| | | | 325 | 13.4 | 97.8 | 2.2 | — | — |
| | | | 350 | 21.0 | 95.0 | 5.0 | — | — |

According to [Table 7], it is confirmed that, when the chlorination reaction of methane was performed by using the sulfated tin oxide catalysts of Examples according to the present invention, the methane conversion was generally increased, and the selectivity to methyl chloride, which is a product, was also sufficiently excellent.

The invention claimed is:

1. A method for producing a reaction product containing methyl chloride ($CH_3Cl$),
wherein the method comprises:
a step a) of forming a mixed solution by mixing an amine reactant and a zirconium precursor containing an oxygen element and dissolving the mixture in a solvent;
a step b) of forming a gel-type product by heating and stirring the mixed solution formed in the step a);
a step c) of forming zirconia ($ZrO_2$) by calcining the gel-type product formed in the step b);
a step d) of preparing sulfated zirconia ($SO_4^{2-}/ZrO_2$) by impregnating the zirconia formed in the step c) with a solution containing a sulfated agent and evaporating the solvent by performing heating;
a step e) of calcining the sulfated zirconia prepared in the step d) at 500 to 800° C. under an air atmosphere and thereby preparing a sulfated zirconia catalyst for chlorination; and
a step f) of performing a chlorination reaction on gaseous reactants consisting of methane ($CH_4$) and chlorine ($Cl_2$) gas under a presence of the sulfated zirconia catalyst for chlorination prepared in the step e).

2. The method of claim 1, wherein the chlorination reaction is performed:
(i) at a temperature of 200 to 550° C.;
(ii) at a molar ratio of methane to chlorine ($Cl_2$) gas of 1/1 to 10/1; and
(iii) at a gas hourly space velocity (GHSV) of each of the reactants of 100 to 3000 cc/g/h.

3. A method for producing a reaction product containing methyl chloride ($CH_3Cl$) by performing a chlorination reaction on gaseous reactants consisting of methane ($CH_4$) and chlorine ($Cl_2$) gas under a presence of a sulfated tin oxide catalyst for chlorination prepared by a preparation method, wherein the preparation method comprises:
a step a) of dissolving a tin precursor in a solvent and inducing hydrolysis of the tin precursor by adding aqueous ammonia until a pH of a solution reaches 7.5 or more;
a step b) of obtaining a solid product by filtering a precipitate obtained by the hydrolysis in the step a);
a step c) of producing tin hydroxide ($Sn(OH)_4$) by drying the solid product obtained in the step b);
a step d) of obtaining a solid product by impregnating the tin hydroxide ($Sn(OH)_4$) produced in the step c) with a solution containing a sulfated agent, stirring the solution and performing filtering;
a step e) of drying the solid product obtained in the step d); and
a step f) of producing sulfated tin oxide by calcining the solid product dried in the step e).

4. The method of claim 3, wherein the chlorination reaction is performed:
(i) at a temperature of 200 to 550° C.;
(ii) at a molar ratio of methane to chlorine ($Cl_2$) gas of 1/1 to 10/1; and
(iii) at a gas hourly space velocity (GHSV) of each of the gaseous reactants of 100 to 3000 cc/g/h.

5. A method for producing a reaction product containing methyl chloride ($CH_3Cl$) by performing a chlorination reaction on a gaseous reactants consisting of methane ($CH_4$) and chlorine ($Cl_2$) gas under a presence of a sulfated zirconia catalyst for chlorination,
wherein a total acid density of the catalyst measured by ammonia temperature-programmed desorption ($NH_3$-TPD) is 8 mmol$NH_3$/g or more, and a proportion of an acid density of a very strong acid site (an acid site at which an acid site desorption temperature is higher than 400° C.) is 80% or more of the total acid density.

6. A method for producing a reaction product containing methyl chloride ($CH_3Cl$) by performing a chlorination reaction on gaseous reactants consisting of methane ($CH_4$) and chlorine ($Cl_2$) gas under a presence of a sulfated tin oxide catalyst for chlorination.

7. The method of claim 5, wherein a content of sulfate ions ($SO_4^{2-}$) in the catalyst is 10.0 wt % or more.

8. The method of claim 6, wherein a content of sulfate ions ($SO_4^{2-}$) in the catalyst is 5.0 wt % or more.

9. The method of claim 6, wherein a total acid density of the catalyst measured by ammonia temperature-programmed desorption ($NH_3$-TPD) is 3.0 mmol$NH_3$/g or more, and
a proportion of an acid density of a very strong acid site (an acid site at which an acid site desorption temperature is higher than 400° C.) is 50% or more of the total acid density.

10. The method of claim 6, wherein a BET specific surface area of the catalyst is 80 to 200 m$^2$/g.

* * * * *